(12) United States Patent
Thompson

(10) Patent No.: US 8,814,774 B2
(45) Date of Patent: Aug. 26, 2014

(54) RADIATION TREATMENT METHOD FOR USE WITH A RADIATION TREATMENT BRA

(76) Inventor: Elizabeth Chabner Thompson, Scarsdale, NY (US)

( * ) Notice: Subject to any disclaimer, the term of this patent is extended or adjusted under 35 U.S.C. 154(b) by 174 days.

(21) Appl. No.: 13/183,139

(22) Filed: Jul. 14, 2011

(65) Prior Publication Data

US 2012/0220811 A1    Aug. 30, 2012

Related U.S. Application Data

(60) Provisional application No. 61/446,278, filed on Feb. 24, 2011.

(51) Int. Cl.
  *A61B 6/00* (2006.01)
  *A41C 3/00* (2006.01)
  *A61N 5/10* (2006.01)

(52) U.S. Cl.
  CPC ....... *A41C 3/0064* (2013.01); *A61N 2005/1097* (2013.01); *A61N 5/1049* (2013.01)
  USPC .......................................................... 600/1

(58) Field of Classification Search
  USPC ............ 600/1–8, 426; 604/20; 378/64, 65, 68
  See application file for complete search history.

(56) References Cited

U.S. PATENT DOCUMENTS 5,769,779 A * 6/1998 Alderson .......................... 600/1
5,820,444 A * 10/1998 McGaughey ................... 450/70
D523,212 S * 6/2006 Iourina .......................... D2/706
2007/0276229 A1* 11/2007 Adler ............................. 600/426
2009/0075562 A1* 3/2009 Lung ............................... 450/58

FOREIGN PATENT DOCUMENTS

GB         772468       4/1957
WO      2008064271 A2    5/2008

OTHER PUBLICATIONS

Goodall, Colin, "PCT Application No. PCT/US2012/025221 International Search Report Apr. 17, 2012", , Publisher: PCT, Published in: PCT.

* cited by examiner

*Primary Examiner* — Christine Matthews
*Assistant Examiner* — Joshua D Lannu
(74) *Attorney, Agent, or Firm* — Kaplan Breyer Schwarz & Ottesen, LLP (57) ABSTRACT

A method for radiation treatment includes adjusting a plurality of adjustable elements on a radiation treatment bra to establish a reference breast geometry and aligning the patient to a radiation treatment machine by projecting a light field through windows provided in the radiation treatment bra during a radiation treatment planning session. To begin actual radiation treatment, the reference breast geometry is reestablished by repeating the original adjustments of the adjustable elements, as necessary. Alignment is re-established by viewing tattoos through the windows in conjunction with the light field.

21 Claims, 10 Drawing Sheets

RADIATION TREATMENT METHOD FOR USE WITH A RADIATION TREATMENT BRA

STATEMENT OF RELATED CASES

This case claims priority of U.S. Provisional Patent Application 61/446,278 filed Feb. 24, 2011 and which is incorporated by reference herein.

FIELD OF THE INVENTION

The present invention relates to radiation oncology in general and, more particularly, to a way to precisely and reproducibly position a breast cancer patient for a radiation treatment session.

BACKGROUND OF THE INVENTION

In 2010, approximately 250,000 women developed invasive or in-situ breast cancer in the United States. The majority of those women sought medical treatment for their disease. Women diagnosed with early stage breast cancer have several options for treatment. The surgical options include mastectomy, with or without reconstruction, or lumpectomy followed by radiation therapy and possibly chemotherapy.

Women choosing lumpectomy and radiation therapy undergo breast-conserving surgery followed by approximately three to six weeks of radiation therapy. The radiation is intended to kill any tumor cells remaining in the breast after surgical removal of the primary tumor. A specialist physician (i.e., radiation oncologist) works in conjunction with a team of physicists, dosimetrists, and radiation-therapy-machine operators ("therapists") to plan and deliver the radiation treatment.

It is particularly important that radiation is delivered to the affected tissue (1) precisely and (2) in reproducible fashion. In particular, the high-energy photons must be delivered to the same planned volume of tissue—the "target"—each session. Care must be taken to avoid irradiating tissues surrounding the target, most importantly lung and heart tissue. Since multiple radiation treatment sessions are required, a reproducible set-up is necessary to ensure that the target site receives the intended cumulative dose of radiation. Receiving the full cumulative dose reduces the patient's risk of developing a local recurrence of the cancer in the treated breast or metastatic spread of the disease.

As such, the best outcomes are achieved when (a) precise radiation treatment parameters are followed, (b) a favorable breast geometry is attained, and (c) a reproducible set-up is established. Satisfying requirements (b) and even more so, (c), can be challenging, as discussed further below.

A woman's breast geometry will change somewhat each time she is on the treatment table. That is, particularly for a large-breasted woman, the shape of the breast is altered as a function of how the breast lies on her chest (e.g., falling off to the side, lying flat, etc.). This complicates the ability to precisely reproduce, during actual treatment, the position/geometry of the breast during the original radiation-planning scan. As a consequence, during an actual treatment, the treatment machine—a very valuable resource—must be idled while time is spent adjusting the patient's position on the treatment table to try, with varying success, to reproduce the original breast geometry and position.

The majority of patients are treated in a supine position with the arm on the affected side "chicken-winged" out of the radiation field over their head. The affected breast can therefore be isolated and treated. The ideal breast geometry for treatment is akin to a tight compact breast mound with no folds of skin.

Women with large, pendulous, ptotic breasts pose challenges for the radiation oncology team. Because of the anatomical shape of the treatment volume and frequent dose variations, acute skin toxicity occurs in "hot spots" such as the axillary tail and the inframammary folds. In addition, breast overhang both in the inferior and/or lateral directions often requires enlargement of the radiation field, which disadvantageously captures larger areas of normal tissue in the radiation tangential fields. Dry and moist desquamation (i.e., raw, peeling areas of skin) can develop in hot spots and in areas where tissue folds upon itself. These problems can necessitate treatment breaks until the skin recovers. These treatment breaks compromise the efficacy of the radiation in killing cancer cells. Furthermore, if a large, pendulous breast falls superiorly, physicians may need to use an inclined breast board (wedged board) to shift the breast. This board must be moved on and off the treatment table before and after each treatment session.

Another treatment strategy for large-breasted women is to place them in the lateral decubitus position with a wedge. Yet a further approach is to have the patient in a prone position wherein their ptotic breast hangs through a "breast board." For many patients, this is a difficult position to achieve and maintain. More importantly, when a patient is in this position, there can be a tradeoff in terms of adequate treatment of the chest wall. Elderly and obese women find the prone set-up position difficult for other health reasons. Additionally, polyvinyl rings are sometimes strapped to large breasts to attain a desired geometry, but it is not possible to reliably reproduce such a set-up. All of these alternative strategies/approaches/positions consume valuable time on the treatment table.

Women with widely spaced, large, pendulous breasts also pose challenges for homogenous treatment. Often, higher-energy radiation is required to achieve homogeneity. Unfortunately, many radiation centers do not have dual-energy machines. Moreover, the higher-energy radiation results in a higher skin dose, which often causes increased skin reaction.

Currently, immobilization devices for women on the treatment table include cradles, plastic molds and netting. There are drawbacks to all such forms of immobilization. Simply put, exact, reproducible, comfortable set-up devices do not exist.

With current treatment regimens, a patient is completely exposed from the waist up while receiving treatment. For many women, this loss of privacy adds to feelings of exposure and vulnerability.

SUMMARY OF THE INVENTION

The present invention provides a way to precisely and reproducibly obtain a desired breast geometry, treatment position, and patient-to-machine alignment for radiation therapy while also enabling the non-affected breast to be moved out of the treatment field.

Some embodiments of the invention provide a radiation treatment brassiere ("bra") that is worn during a radiation treatment session. In the illustrative embodiment, the bra includes a clear medial window (or both clear medial and lateral windows), sheer substantially "see-through" cup material, and multiple adjustment elements. The bra is devoid of metal and uses hook and loop fastener (e.g., VELCRO®, etc.). The bra can be worn for use with all treatment machines without causing bolus effect. The bra is undetectable during CT scan.

The clear medial and lateral windows enable the physician and therapist to view and mark tattoos, as well as the midline and treatment parameters, as created by the light field that is projected by the treatment machine onto the patient's chest. The sheer cup material allows the physician and therapists to mark the bra, as necessary (e.g., using indelible marker, etc.) and to view the breast, scars, or alignment wires and tattoos.

Multiple adjustable elements, which can be (but are not necessarily) implemented as closures, enable the position of the breast to be adjusted to achieve a desired reference breast geometry during a radiation treatment planning session. This is achieved by appropriately tightening or loosening the various adjustable elements, thereby establishing a "reference setting" for each such adjustable element. In some embodiments, the adjustable elements include: (1) a medial (central) element, disposed between the breast cups; (2) two lateral elements, disposed at the interface of each cup and the cooperating end of the back band; and (3) two superior elements, disposed within each shoulder strap. In some other embodiments, fewer adjustable elements are used.

In the illustrative embodiments, the adjustable elements are closures, at least one of which is released to enable the bra to be removed or put-on. For the one or more closures that are to be released, the previously established reference setting, which is indicated via some type of measurement tool, scale, etc., is memorialized (e.g., recorded in the patient's chart, etc.). This enables a technician to reset all released closures to their established reference settings prior to a radiation treatment session. Since the reference setting for each adjustable element establishes the reference breast geometry, the reference breast geometry is re-established for each radiation treatment session by simply resetting each released adjustable closure to its reference setting.

In some further embodiments, the bra includes a closure that is not intended to establish the reference breast geometry but, rather, is used to remove the bra or put it on. For such embodiments, once the bra is appropriately adjusted via the adjustable elements, the closure is used for taking the bra off or putting it on (e.g., for the next treatment session). As a consequence, the adjustable elements need not be closures, and if they are closures, they do not need to be re-set (since they do not to be released to remove the bra). In some embodiments, this closure is located near the mid-point of the back-band.

Thus, a radiation treatment bra in accordance with the present teachings can reliably reproduce the desired breast geometry prior to each radiation treatment session. The radiation treatment bra also provides an ability to move the non-treated breast laterally to avoid, to extent possible, placing medial tissue of the contralateral breast in the treatment field.

Some other embodiments of the invention provide a method for radiation therapy that includes establishing a reference breast geometry using a radiation treatment bra in accordance with the present invention.

DETAILED DESCRIPTION

Figure 1A:
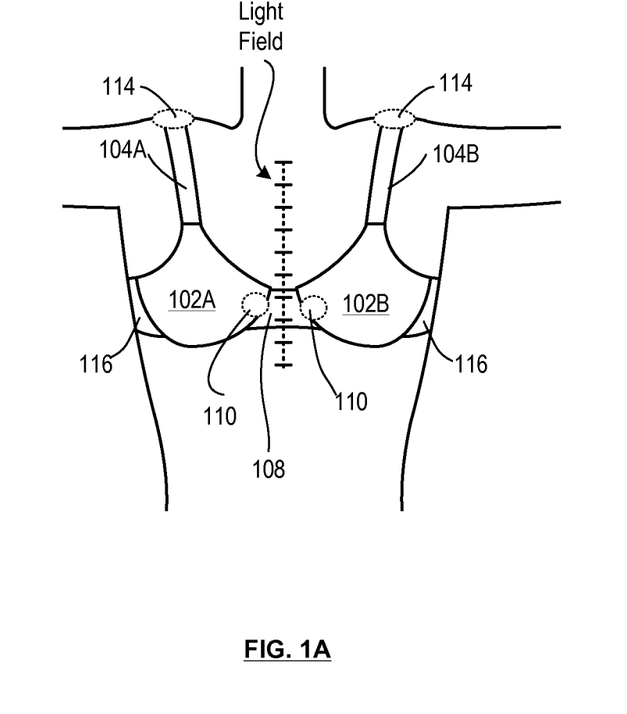
FIG. 1A depicts a front view of radiation treatment bra 100 in accordance with the illustrative embodiment of the present invention.
Figure 1B:
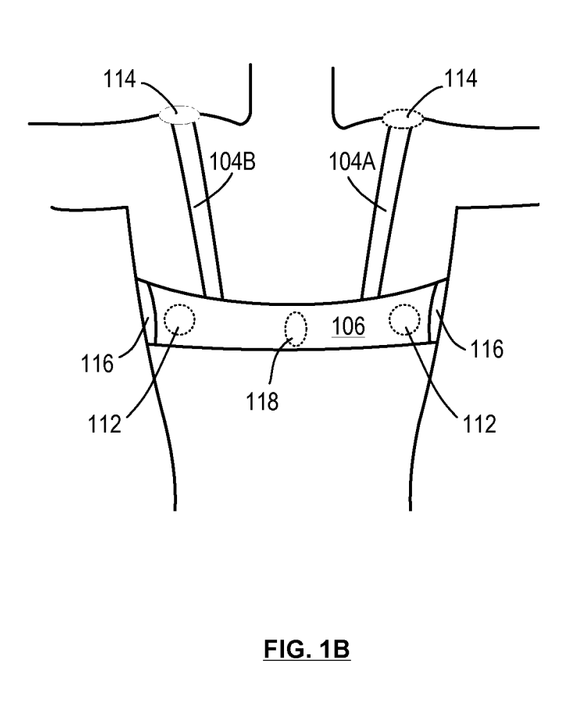
FIG. 1B depicts a back view of radiation treatment bra 100.

FIGS. 1A and 1B depict respective front and back views of radiation treatment bra 100 in accordance with the illustrative embodiment of the present invention. Like virtually all bras, embodiments of the radiation treatment bra disclosed herein include breast cups 102A and 102B, shoulder straps 104A and 104B, and back band 106.

For use in conjunction with the present invention, cups 102A and 102B advantageously comprise a sheer stretch material, such as, without limitation, a sheer version of LYCRA® brand spandex fiber. The material is preferably sufficiently sheer so that features on the breast (e.g., scars, tattoos, etc.) are visible. Shoulder straps 104A and 104B comprise a resilient, elastic material, such as, without limitation, LYCRA® brand spandex fiber. Back band 106 comprises a resilient, elastic material, such as, without limitation, LYCRA® brand spandex fiber. Other materials, known to those skilled in the art, may suitably be used for the cups, shoulder straps and back band. It is important, however, that the materials do not include anything that will scatter or otherwise substantially attenuate the radiation treatment beam or add bolus effect.

It is to be understood that the proportions of radiation treatment bra 100 shown in FIGS. 1A and 1B, as well as the proportions of the various embodiments of the bras depicted in other Figures, are provided by way of illustration, not limitation. For example, deviations from the width of shoulder straps 104A and 104B, the width of back band 106, the coverage provided by cups 102A and 102B, etc., are acceptable as long as they do not compromise the functionality of the radiation treatment bra, as disclosed herein. Furthermore, it is to be understood that the radiation treatment bras disclosed herein can incorporate industry-standard features and design elements, such as a "racer-back" configuration for the shoulder straps, etc., as long as such features and design elements do not compromise radiation-treatment-bra functionality, as disclosed herein.

The radiation treatment bra depicted in FIGS. 1A and 1B further includes medial window 108, lateral windows 116, medial adjustment element(s) 110, lateral adjustment element(s) 112, superior adjustment element(s) 114, and non-participating closure 118. Not all of the various features depicted in FIGS. 1A and 1B are present in all embodiments of the radiation treatment bra. Specific embodiments of bras including some or all these features are described later in this specification in conjunction with FIGS. 2 and 4-8. A radiation treatment bra showing additional features is discussed in conjunction with FIGS. 9A and 9B.

With continued reference to FIGS. 1A and 1B, medial window 108 is disposed between cups 102A and 102B. Medial window 108 comprises a clear/transparent material that is free of metals or other constituents that will scatter or substantially attenuate the radiation treatment beam or cause bolus effect. In some embodiments, medial window 108 comprises a clear thermoplastic material, such as Clear-Fit TPU brand thermoplastic polyurethane, commercially available from Fulflex, Inc. of Brattleboro, Vt.

Medial window 108 enables a light field, which originates from the radiation treatment machine, to be projected onto a patient's chest and viewed. During a radiation planning session, using the light field is used as a guide, temporary and then permanent marks (i.e., tattoos) are placed on the patient's chest to establish the requisite alignment with respect to the treatment machine. The tattoos are later used to re-establish the requisite alignment for actual radiation treatment sessions. When the material used for medial window 108 is suitably selected, the tattoos can be made through the medial window without damaging the window or compromising the alignment. One such suitable material is the aforementioned Clear-Fit TPU brand thermoplastic polyurethane.

The width of medial window 108 is at least about 3 centimeters, which will accommodate the lateral extent of the light field projected by the radiation treatment machine. The light field may extend downward from the patient's clavicular depression for about 25 centimeters along the mid-line of the torso. For this reason, a radiation treatment bra in accordance with the present invention does not obscure a view of the patient's skin along the midline of the torso. As shown in FIG. 1A, a portion of the light field would be obscured if not for the presence of medial window 108.

The radiation treatment bra depicted in FIGS. 1A and 1B also includes left and right lateral windows 116. One window is disposed between cup 102A and an end of back band 106; the other is disposed between cup 102B and the other end of back band 106. The lateral windows are situated so that when the bra is in use, the lateral windows are positioned beneath the patient's axilla (i.e., arm pits). The lateral windows extend at least about 5 centimeters "back" from the lateral edge of each cup. The purpose for the lateral windows is to enable radiation treatment personnel to create and view alignment tattoos on the skin in those regions. Like the medial window, the lateral windows comprise a transparent material that will not scatter or substantially attenuate the radiation beam.

As noted in the Background section of this specification, it is particularly important that treatment radiation is delivered to the same planned volume of tissue during each radiation treatment session. Doing so is complicated by the fact that a woman's breast geometry can change somewhat each time she is on the treatment table. Also, over the three- to six-week course of therapy, there can be swelling and weight gain or loss that might shift the breast and change its volume. This is particularly problematic for a large-breasted woman, wherein the shape of the breast is altered as a function of how the breast lies on her chest. This variability in breast geometry complicates the ability to precisely reproduce, during actual treatment, the position/geometry of the breast as it existed during the original radiation-planning scan.

Adjustable elements 110, 112, and 114 are used adjust the geometry and position of a breast to establish a reproducible reference breast geometry for use during radiation treatment sessions. More particularly, during the radiation planning session, adjustable elements 110, 112, and 114 are adjusted (e.g., tightened or loosened, etc.) until breast geometry/position is considered to be at a practical optimum for treatment. That practical optimum, which is determined by oncology/radiation professionals in conjunction with radiation simulations, is a position/shape for the breast that provides the best compromise between irradiating the target tissue and not surrounding tissues. As used in this specification and the included claims, the term "reference breast geometry" refers to this practical optimum for the position/shape of the breast. As used in this specification and the included claims, the terms "adjustable element" or "adjustable closure" mean a fixture, arrangement, etc., that is capable of adjusting the geometry and position of a breast by changing the force applied by parts of the bra, such as the shoulder straps, the back band, etc., on the breast cups. The adjustable elements/closures are also used to position the non-affected breast out of the treatment field, to the extent possible.

As depicted in FIGS. 1A and 1B, medial adjustable element(s) 110 are disposed proximal to cups 102A and 102B. Lateral adjustable element(s) 112 are disposed proximal to each of back band 106. Superior adjustable element(s) 114 are situated along shoulder straps 104A and 104B such that when the bra is in use, these elements lie near the top of a wearer's shoulder.

As previously indicated, the best outcomes for radiation treatment are attained when the reference breast geometry is reproduced for each radiation treatment session. Reference breast geometry is re-established in any one of several ways, the choice of which depends, in part, on the form of the adjustable elements. In particular, in some embodiments, adjustable elements 110, 112, and 114 are embodied as "closures" that can be released to enable a patient to remove the bra. In some other embodiments, the adjustable elements are not embodied as closures, but rather as a feature that simply provides an adjustment function, such as the well known "adjustable slider," etc. Regardless of its structure, the adjustable element must comprise a material that will not scatter the treatment radiation or cause a bolus effect.

In embodiments in which the adjustable elements are closures, at least some of which are used to "open" the bra to remove it or put it on, the adjustable elements include a measurement tool (e.g., scale, etc.) that provides an indicium of fit. As used in this specification, including the claims, the term "indicium of fit" refers to a measure or indication of the tightness or snugness of each adjustable element, as determined from a measurement tool, scale, etc., that is associated with the adjustable element.

Once the reference breast geometry is attained by adjusting the adjustable elements, the setting for each adjustable element that establishes the reference breast geometry—which is known as the "reference setting"—is read from the scale that provides the indicium of fit and can be noted, as required, in the patient's chart, etc. This enables a technician or patient to re-establish the reference breast geometry by simply adjusting each adjustable element to its reference setting before each treatment session, as necessary.

Another way to reproduce the reference breast geometry, once established, is to use a closure, such as closure 118, which is not used to establish the reference breast geometry. In bra 100 depicted in FIGS. 1A and 1B, closure 118 (hereinafter referenced as a "non-participating closure") is disposed near the mid-point of back band 106. Non-participating closure 118, which can be (but is not necessarily) non-adjustable, permits bra 100 to be removed without having to release any of the adjustable (and hence reference-breast-geometry-establishing) elements 110, 112, and 114, to the extent such adjustable elements are embodied as closures.

Figure 2:
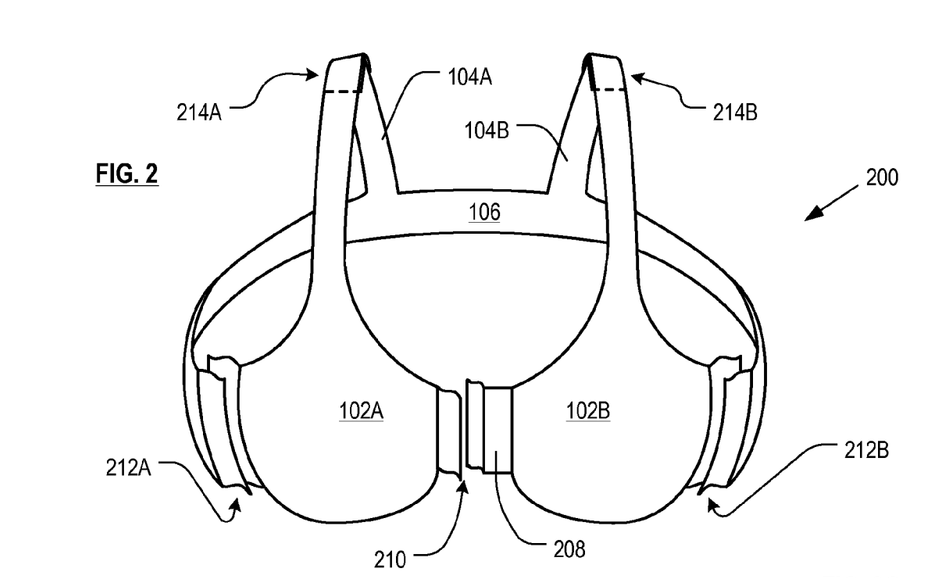
FIG. 2 depict radiation treatment bra 200, wherein the bra includes adjustable elements that are embodied as closures.

Consider, for example, an embodiment in which the adjustable elements are embodied as "closures," and are the only closures on the bra, as in bra 200 depicted in FIG. 2. To remove this bra, or put it on, one or more of the closures would have to be released and then necessarily reset for the next radiation treatment session. But when the bra includes non-participating closure 118, the adjustable "closures," once set to establish the reference breast geometry, need not be released. Rather, using non-participating closure 118, every time the patient puts the bra on before a treatment session, the reference breast geometry will be "automatically" re-established; no re-setting of the adjustable elements is required. As used in this specification, including the claims, the term "non-participating closure" refers to a closure that is not involved in establishing the reference breast geometry. Rather, such a closure is used to simply open the bra to enable a patient to remove it after a radiation treatment session.

It will be appreciated that the use of non-participating closure 118 enables adjustable element(s) 110, 112, and 114 to be embodied as something other than closures.

Although a non-participating closure is not involved in establishing the reference breast geometry through adjustment, that closure can be an adjustable closure (as long as the closure can be released without altering its state of adjustment). After reading this disclosure, those skilled in the art will know how to add a non-participating closure in other locations on a radiation treatment bra in accordance with the present teachings. For example, the non-participating closure can be situated between the cups (i.e., in place of adjustable closure 110). In such an embodiment, the non-participating closure must not obscure the medial window.

After reading the present disclosure, those skilled in the art will know how to incorporate adjustable elements, for obtaining a reference breast geometry, which are not closures. For example, an adjustable slider can be used.

FIG. 2 depicts radiation treatment bra 200 in accordance with the present invention. Radiation treatment bra 200 includes breast cups, shoulder straps, and a back band. In bra 200, adjustable elements 110, 112, and 114 (see FIGS. 1A and 1B) are embodied as adjustable closures. In particular, they are embodied as adjustable medial closure 210, adjustable lateral closures 212A and 212B, and adjustable superior closures 214A and 214B.

As depicted in the embodiment shown in FIG. 2, shoulder straps 104A and 104B each comprise two segments; an anterior segment that couples to one of the breast cups and a posterior segment that couples to back band 106. In preferred embodiments, the anterior segment overlies the posterior segment when brought together to "close" closure 214A and 214B. (See, e.g., FIG. 3C).

In radiation treatment bra 200, each of the adjustable closures comprise paired strips of hook-and-loop fastener, such as VELCRO® brand hook-and-loop fastener, available from Velcro Co. of Manchester, N.H. In other embodiments, other types of fastening systems may be used, as long as the fastening systems comprise materials that will not scatter radiation.

Since bra 200 does not include non-participating closure 118, at least some of the adjustable closures must be released to remove the bra. As a consequence, it is important that the reference setting is memorialized for at least those closures that will be released (to remove the bra).

Figure 3A:
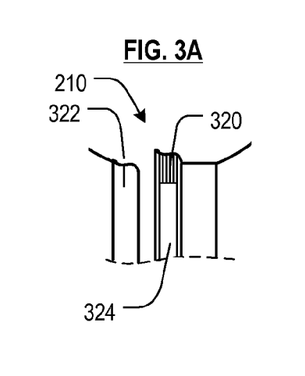
FIG. 3A depicts further detail of the medial adjustable element of bra 200, wherein the adjustable element comprises a scale that provides an indicium of fit in accordance with the present invention.
Figure 3B:
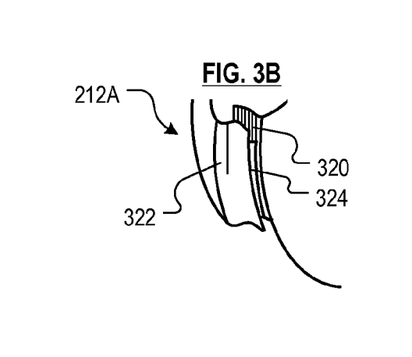
FIG. 3B depicts further detail of the lateral adjustable element of bra 200, wherein the adjustable element comprises a scale that provides an indicium of fit in accordance with the present invention.
Figure 3C:
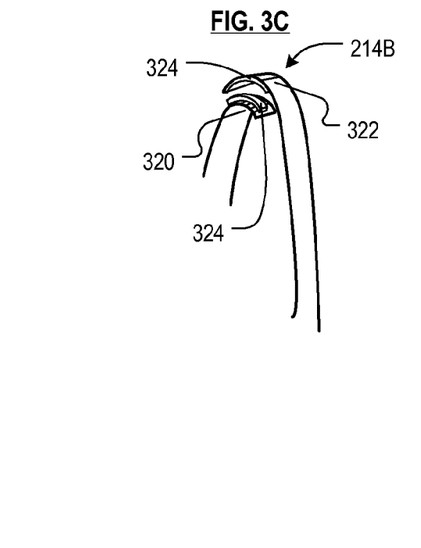
FIG. 3C depicts further detail of the superior adjustable element of bra 200, wherein the adjustable element comprises a scale that provides an indicium of fit in accordance with the present invention.

FIGS. 3A through 3C depict an embodiment of a scale that provides an indicium of fit for use with respective medial adjustable closure 210, lateral adjustable closures 212A and 212B and superior adjustable closures 214A and 214B. These adjustable closures comprise two portions, wherein each closure portion comprises a material that supports a strip of hook-and-loop fastener 324. The segment of hook-and-loop fastener 324 on one of the closure portions is obscured in FIGS. 3A and 3B.

In FIGS. 3A through 3C, the scale that provides the indicium of fit comprises a plurality of lines 320, which is disposed on one of two closure portions. A single line 322, which acts as an indicator, is disposed on the other of the two closure portions.

Each line 320 has associated with it an identifier, such as a number or letter (not depicted). When the two closure portions are brought together to engage one another, the indicator line 322 on one of the closure portions will align with one of the lines 320 in the scale. The particular line 320 that aligns with line 322 provides the "setting" of the adjustable closure. When the adjustable closures 210, 212A/212B, and 214A/214B are set such that they provide the reference breast geometry, the setting is the "reference setting." The identifier associated with the respective "aligned" line 320 is recorded in the patient's chart.

In other embodiments, rather than using an indicator line 322 on one of the closure portions, the leading edge of that closure element is used as an indicator. After reading the present disclosure, those skilled in the art will be able to devise other measurement arrangements suitable for providing a setting that identifies the relative positions of the two closure elements.

As an alternative to using two paired sections of hook-and-loop fastener, one section of such material can be used in conjunction with a "hook-compatible fabric" (i.e., VELCRO® receptive). In other words, the hook-and-loop fastener will simply "stick" to the fabric. Such fabric is commercially available from Darlington Fabrics of Westerly, R.I., and others. The measurement tool (e.g., scale, etc.) can be printed directly onto the fabric.

Another approach for establishing a reproducible, reference breast geometry, which is especially useful when the adjustable elements are embodied as closures, is to place a "mark" on the closure portions of the adjustable closures after they are set to provide the reference breast geometry. The mark, which is placed on one or both portions of each adjustable closure, records the amount of overlap of the two closures. The mark(s) can be made, for example, with indelible marker. This enables the reference breast geometry to be reproduced each time the bra is worn by simply adjusting the adjustable elements in accordance with the marks. In this approach, there is no scale, per se; rather, only an indication that provides the reference setting. Furthermore, the act of "marking" simultaneously creates the reference setting and memorializes (i.e., "notes" or records) it.

Regardless of the approach taken, what is important is that state (i.e., the reference setting) of the adjustable closure can be reliably reproduced.

It will be appreciated that in the embodiments depicted in FIGS. 3A through 3C, the scale is simply a measure of the extent to which the two closure portions overlap one another. To the extent the adjustable elements have a different structure, the form of the scale that provides the indicium of fit may be different. After reading the present disclosure, those skilled in the art will be able to develop an appropriate scale as a function of the structure/arrangement of the adjustable element.

Figure 4:
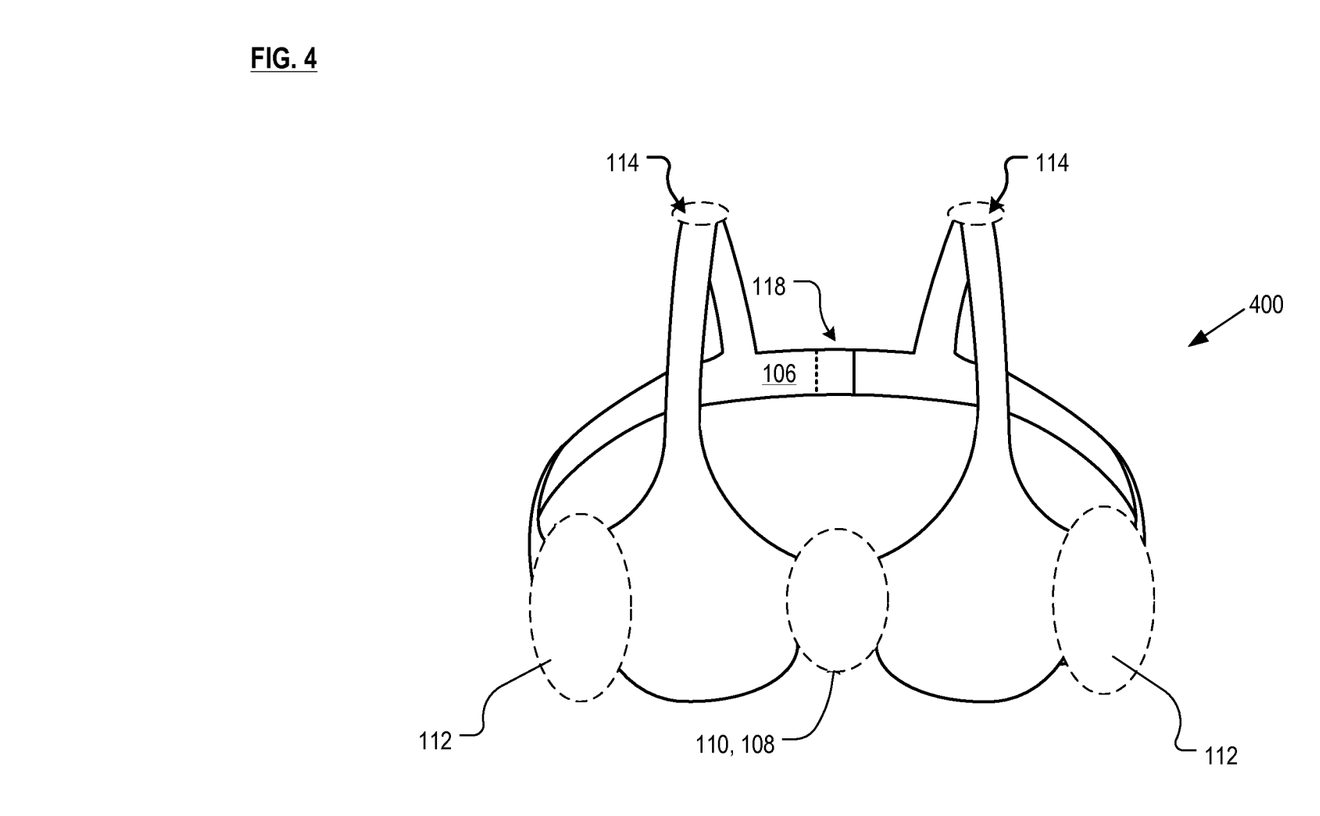
FIG. 4 depicts radiation treatment bra 400, wherein the bra further includes a non-participating closure.

FIG. 4 depicts radiation treatment bra 400. This bra is structured similar to bra 200, and includes breast cups, shoulder straps, back band, medial window 108, a medial adjustable element 110, lateral adjustable elements 112, and superior adjustable elements 114.

Unlike bra 200, radiation treatment bra 400 includes non-participating closure 118, which is disposed near the midpoint of back band 106. Since bra 400 includes non-participating closure 118, the adjustable elements need not be (but can be) closures (e.g., like adjustable closures 210, 212A/212B, and 214A/214B) since they do not need to be released to remove the bra. The non-participating closure can comprise a plastic clasp, hook-and-loop fastener, etc. Regardless of structure, the non-participating closure will preferably not scatter treatment radiation.

Figure 5:
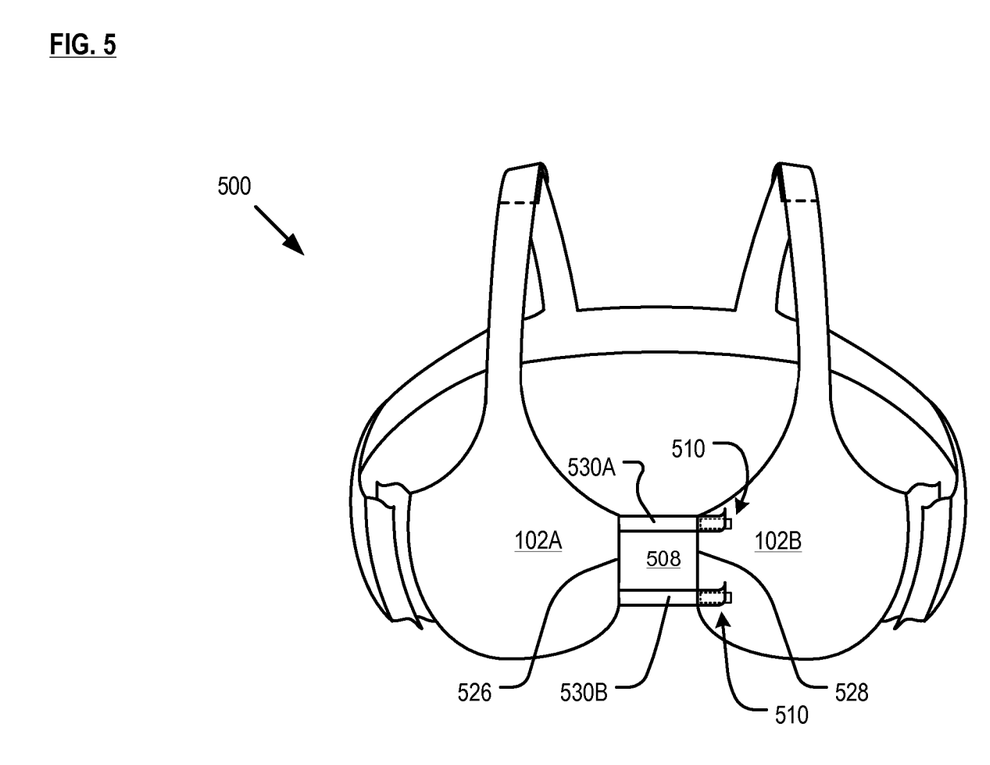
FIG. 5 depicts radiation treatment bra 500, including an alternative configuration for the medial window and medial adjustable elements.

FIG. 5 depicts radiation treatment bra 500. This bra is structured similar to bra 200 and includes breast cups, shoulder straps, back band, a medial adjustable element, lateral adjustable elements, and superior adjustable elements, wherein the adjustable elements are configured as closures.

Since, in the embodiment depicted in FIG. 5, bra 500 does not include a non-participating closure, the adjustable elements are configured as closures. The lateral and superior adjustable closures of bra 500 are the same as those for bra 200 and 200, but medial adjustable closure 510 of bra 500 is configured differently than medial adjustable element 210 of bra 200.

In particular, medial adjustable element 510 comprises two spaced-apart, horizontally-oriented strips 530A and 530B of transparent material that will not scatter or substantially attenuate the radiation beam. The strips are attached to inner edge 526 of cup 102A. Strip 530A is attached relatively nearer to the top of inner edge 526 and strip 530B is attached relatively nearer to the bottom. A section of hook-and-loop fastener (not depicted) is disposed at the free end of each of strips 530A and 530B. Adjustable element 510 includes two further sections of hook-and-loop fastener, which are each disposed near inner edge 528 of cup 102B, one section closer to the top of the inner edge and the other closer to the bottom. These two sections of hook-and-loop fastener are positioned to receive and engage the sections of hook-and-loop-fastener that are disposed near the respective free ends of strips 530A and 530B.

Medial window 508 is defined between strips 530A and 530B. Like the various medial windows depicted for other embodiments of the radiation treatment bra, medial window 508 permits projecting the light field onto the midline of a patient's chest, viewing the light field, and creating tattoos, as well as viewing any such tattoos or other marks that are placed along the midline of the chest in the region between the cups. Unlike bra 200, which includes a medial window that is formed of a transparent material, in bra 500, medial window 508 is simply open space (i.e., no material). The distance between inner edges 526 and 528 of respective cups 102A and 102B is at least about 3 centimeters, which will accommodate the lateral extent of the light field projected by the radiation treatment machine.

In some further embodiments of radiation bra 500, a scale that provides an indicium of fit, such as depicted in FIGS. 3A through 3C, is used in conjunction with adjustable elements of bra 500, including medial adjustable element 510. In some additional embodiments, radiation bra 500, with or without such a scale, includes non-participating closure 118, which may be situated along the mid-point of back band 106 as depicted in bra 400, or situated elsewhere. In embodiments that include non-participating closure 118, the adjustable elements need not (but can) be configured as closures; that is, they need not be releasable.

Figure 6:
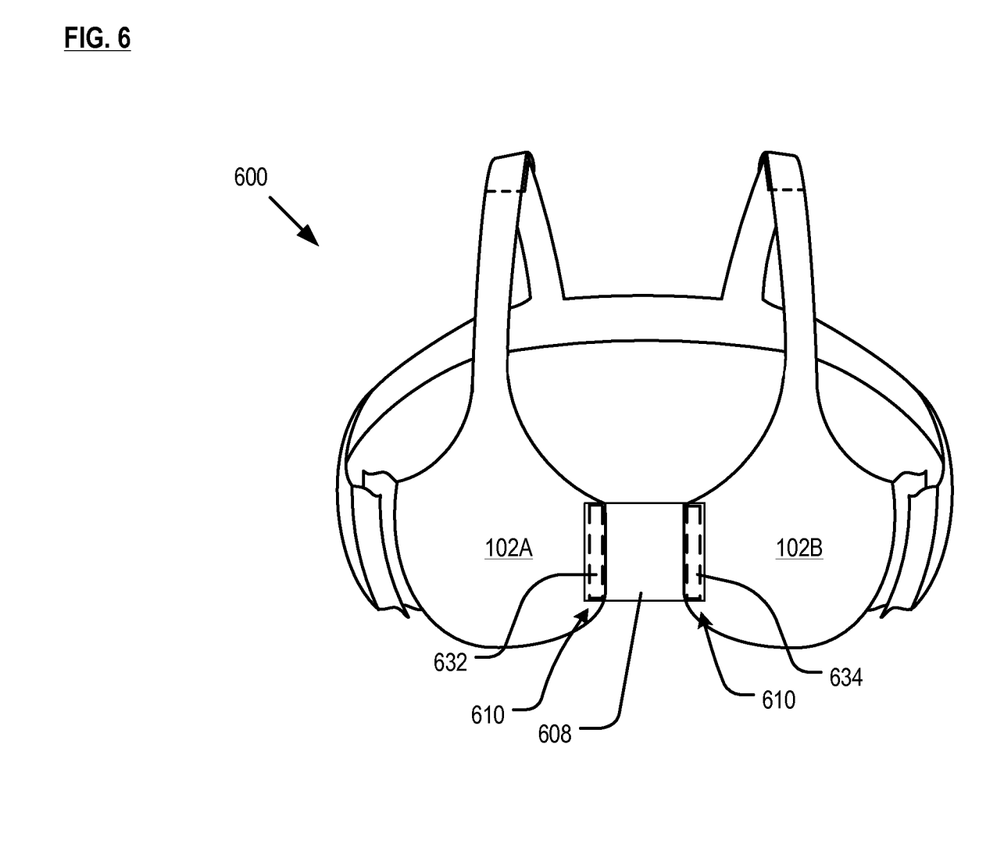
FIG. 6 depicts radiation treatment bra 600, including an alternative configuration for the medial window and medial adjustable elements.

FIG. 6 depicts radiation treatment bra 600. This bra is structured similar to bra 500, and includes breast cups, shoulder straps, back band, a medial adjustable element, lateral adjustable elements, and superior adjustable elements.

Since, in the embodiment depicted in FIG. 6, bra 600 does not include a non-participating closure, the adjustable elements are configured as closures. The lateral and superior adjustable closures of bra 600 are the same as those for bra 500, but medial adjustable closure 610 of bra 600 is configured differently than medial adjustable closure 510 of bra 500.

The lateral and superior adjustable elements of bra 600 are the same as those for bra 400, but medial adjustable closure 610 of bra 600 is configured differently than medial adjustable closure 510 of bra 500. In fact, medial adjustable closure 610 includes medial window 608.

Medial adjustable element 610 comprises two strips 632 and 634 of hook-and-loop fastener, which are disposed near respective inner edges of cups 102A and 102B. As indicated above, medial adjustable element 610 also includes medial window 608, which comprises a transparent material that will not scatter or substantially attenuate the radiation treatment beam. Two strips of hook-and-loop fastener (not depicted) are attached to one face of medial window 608, near the edges thereof. The strips of hook-and-loop fastener on medial window 608 are positioned to engage strips 632 and 634 of hook-and-loop fastener that are disposed near the inner edges of the cups.

When medial adjustable closure 610 is closed, the distance between the inner edges of respective cups 102A and 102B is at least about 3 centimeters to accommodate the lateral extent of the light field projected by the treatment machine.

In some further embodiments of radiation bra 600, a scale that provides an indicium of fit, such as depicted in FIGS. 3A through 3C, is used in conjunction with the adjustable elements of bra 600, including medial adjustable element 410. In some additional embodiments, radiation bra 600, with or without the scale, includes non-participating closure 118. The non-participating closure can be disposed near the mid-point of back band 106 as in bra 400, or disposed elsewhere. In embodiments that include non-participating closure 118, the adjustable elements need not (but can) be configured as closures; that is, they need not be releasable.

Figure 7:
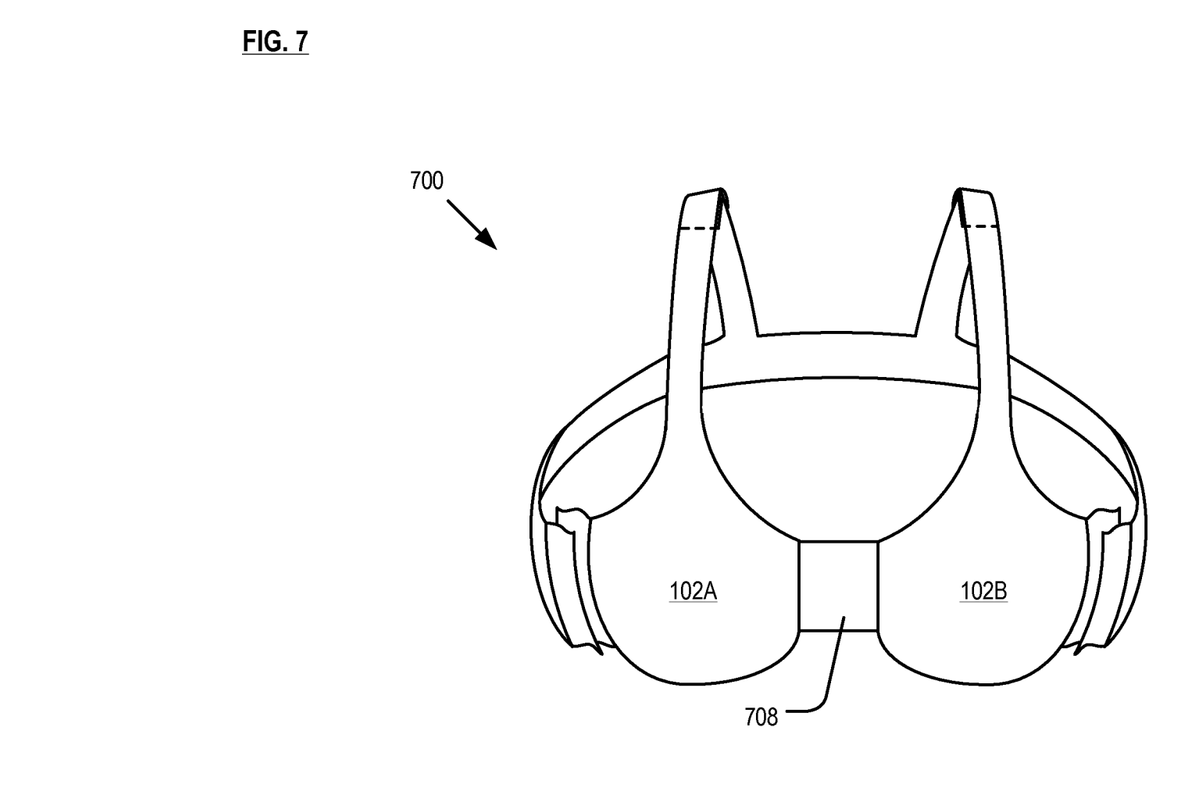
FIG. 7 depicts radiation treatment bra 700, including an alternative configuration for the medial window and non medial adjustable elements.

FIG. 7 depicts radiation treatment bra 700. This bra is structured similar to bra 600, and includes breast cups, shoulder straps, back band, lateral adjustable elements, and superior adjustable elements. Since, in the embodiment depicted in FIG. 7, bra 700 does not include a non-participating closure, the adjustable elements are configured as closures. Unlike bra 600 and other bras disclosed herein, radiation bra 700 does not include a medial adjustment element, embodied as a closure or otherwise.

Radiation bra 700 includes medial window 708, which is disposed between the inner edges of cups 102A and 102B. Medial window 708 comprises a transparent material that will not scatter or substantially attenuate the radiation beam or cause a bolus effect. Like the various medial windows depicted for other embodiments of the radiation treatment bra, medial window 708 permits projecting the light field onto the midline of a patient's chest, viewing the light field, and creating tattoos, as well as viewing any such tattoos or other marks that are placed along the midline of the chest in the region between the cups. The width of medial window 708 (i.e., the distance between the inner edges of cups 102A and 102B) is at least about 3 centimeters for that purpose.

In some further embodiments of radiation bra 700, a scale providing an indicium of fit, such as depicted in FIGS. 3A through 3C, is used in conjunction with the lateral and superior adjustable elements. In some additional embodiments, radiation bra 700, with or without such a scale, includes non-participating closure 118, which may be disposed near the mid-point of back band 106 as in bra 400, or disposed elsewhere. In embodiments that include non-participating closure 118, the adjustable elements need not (but can) be configured as closures; that is, they need not be releasable.

Figure 8:
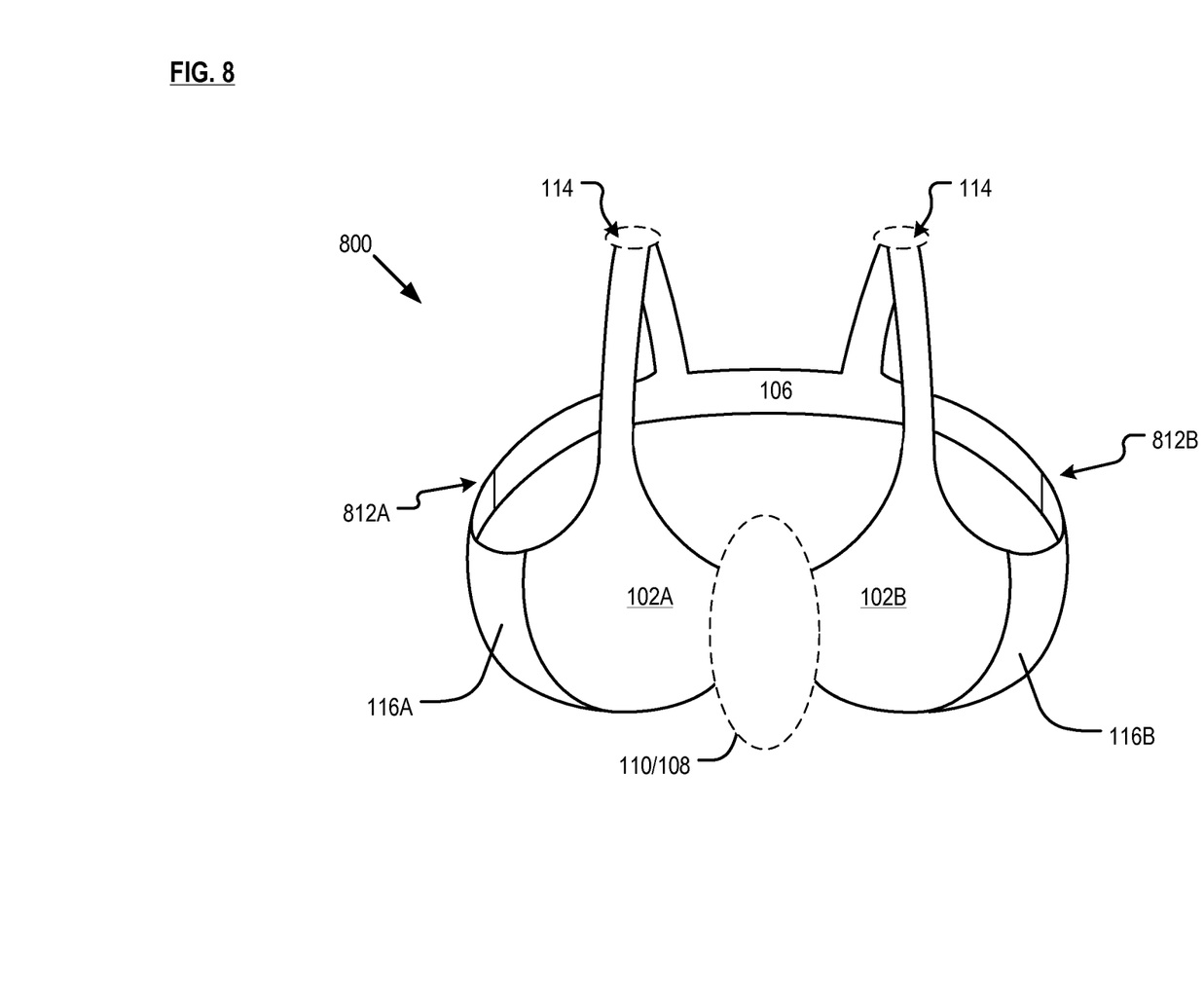
FIG. 8 depicts radiation treatment bra 800, including lateral windows.

FIG. 8 depicts radiation treatment bra 800. This bra is structured similar to other embodiments of the radiation treatment bra, and includes breast cups, shoulder straps, and a back band. And bra 800 includes any version of superior adjustable elements 114 and any version of medial adjustable element 110 (e.g., 210, 510, 610, etc.) and any version of medial window 108 (e.g., 208, 508, 608, 708, etc.). But unlike bras 200 and 400 through 700, radiation bra 800 includes two lateral windows 116A and 116B. Window 116A is disposed between cup 102A and an end of back band 106. Window 116B is disposed between cup 102B and an end of back band 106.

The lateral windows are situated so that when the bra is in use, the lateral windows are positioned beneath the axilla (i.e., arm pits). The lateral windows extend at least about 5 centimeters "back" from the lateral edge of each cup. The purpose for the lateral windows is to enable radiation treatment personnel to create and view alignment tattoos on the skin in those regions. The alignment process is similar to that previously discussed, except that rather than projecting the light field onto a patient's chest, it is projected onto a side of the patient's torso through one of the lateral windows. Like the medial windows previously discussed, lateral windows 116A and 116B comprise a transparent material that will not scatter or substantially attenuate the radiation beam. When the material is suitably selected, such as the aforementioned Clear-Fit TPU brand thermoplastic polyurethane, tattoos can be created through the lateral windows.

Radiation treatment bra 800 also includes lateral adjustment elements 812A and 812B, which are disposed along back band 106 proximal to the lateral windows. The lateral adjustment elements can be configured like lateral adjustment elements 212A and 212B of bra 200, for example, but shifted along the back-band away from the lateral edge of the cups to accommodate the presence of the lateral windows.

In some further embodiments of radiation bra 800, a scale that provides an indicium of fit, such as depicted in FIGS. 3A through 3C, is used in conjunction with the medial, lateral, and superior adjustable elements. In some additional embodiments, radiation bra 800, with or without such a scale, includes non-participating closure 118, which may be disposed near the mid-point of back band 106 as in bra 400, or disposed elsewhere. In embodiments that include non-participating closure 118, the adjustable elements need not (but can) be configured as closures; that is, they need not be releasable.

It is notable that even in embodiments of the radiation treatment bra that do not include a non-participating closure, some of the adjustable elements can be configured as closures and some not. For example, in some embodiments, the medial adjustable element is configured as a closure but the lateral and superior adjustable elements are not. In some other embodiments, the superior adjustable elements are configured as a closure but the lateral and medial are not. And so forth.

Figures 9A, 9B:
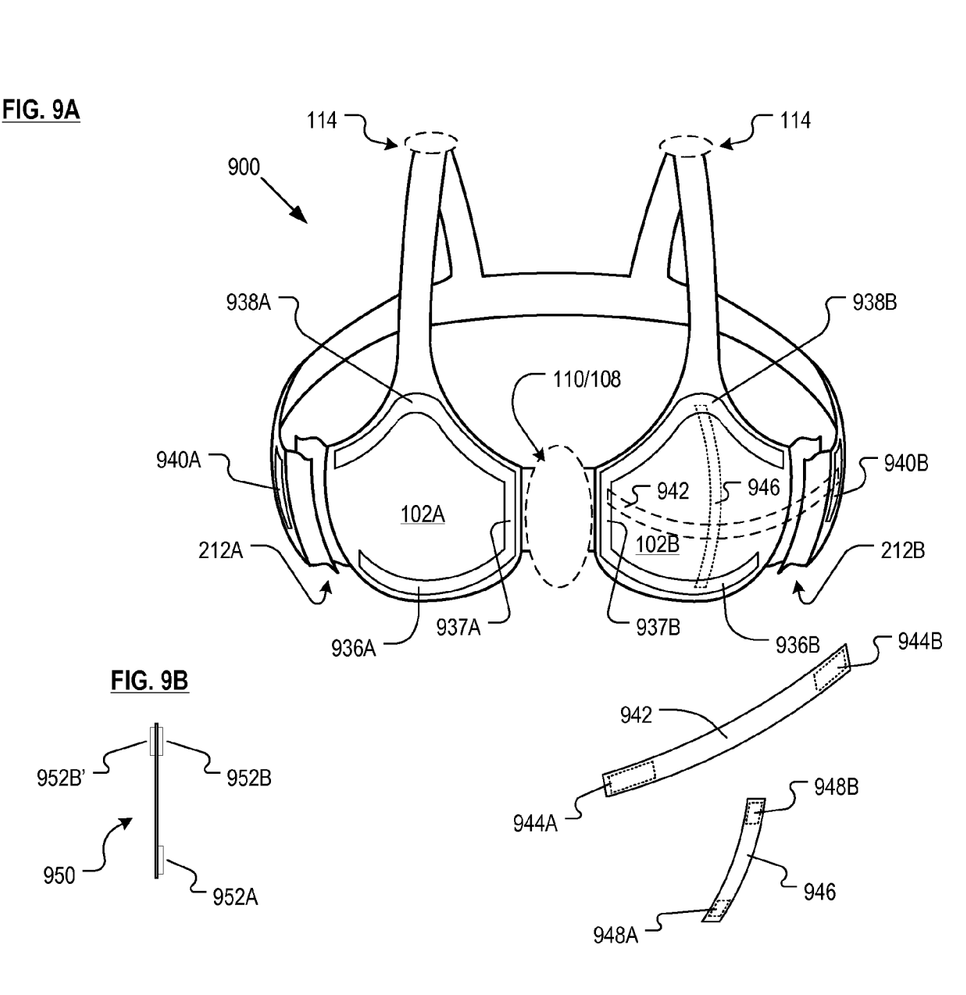
FIG. 9A depicts radiation treatment bra 900, including breast-supporting slings.
FIG. 9B depicts an alternative embodiment of a sling for use with the embodiment of FIG. 9A.

FIG. 9A depicts radiation treatment bra 900. This bra is structured similar to other embodiments of the radiation treatment bra, and includes breast cups, shoulder straps, and a back band. And bra 900 includes any version of superior adjustable elements 114 and any version of medial adjustable element 110 (e.g., 210, 510, 610, etc.) and any version of medial window 108 (e.g., 208, 508, 608, 708, etc.). Bra 900 further includes lateral closures, which in the embodiment depicted in FIG. 9A, are embodied as adjustable lateral closures 212A and 212B of Bra 200 (see, FIG. 2).

Bra 900 also includes one or more slings 942 and 946 that detachably couple to either of cups 102A and 102B and serve a purpose similar to an "underwire;" that is, they provide "lift." A metal underwire cannot be used in the radiation treatment bras disclosed herein because it would scatter treatment radiation. A plastic "underwire" could be used, but, as will become apparent, the use of slings provides greater adjustability.

In the illustrative embodiment, bra 900 includes sections 936A, 936B, 937A, 937B, 938A, 938B, 940A, and 940B of hook-compatible fabric. Sections 936A, 937A and 938A are disposed on cup 102A and sections 936B, 937B, and 938B are disposed on cup 102B. Furthermore, section 940A is disposed near the end of back band 106 proximal to lateral closure 212A and section 940B is disposed near the end of back band 106 proximal to lateral closure 212B. These sections of hook-compatible fabric can be sewn on to the bra or attached via other appropriate techniques.

FIG. 9A depicts two slings: sling 942 and sling 946. Sling 942 is the longer of the two slings, having a length of about 18 to about 25 centimeters. Sling 946 has a length of about 8 to about 18 centimeters. The slings have a width of about 25 millimeters. In some embodiments, the slings comprise a strip of transparent material that will not scatter or substantially attenuate the radiation beam, such as Clear-Fit TPU brand thermoplastic polyurethane. Strips 944A and 944B of hook-and-look fastener are disposed at each end of sling 942. Strips 948A and 948B of hook-and-look fastener are disposed at each end of relatively shorter sling 946. The slings couple to the bra by mating the strips of hook-and-loop fastener on the sling to the sections of hook-compatible fabric on the bra.

In use, and using cup 102B as an example, a sling (of appropriate length) will typically be oriented in one of the following ways:
   medial (937B) to lateral (940B);
   inferior (936B) to lateral (940B); and
   inferior (936B) to superior (938B).

A sling, such as sling 942 or 946, can be coupled anywhere along inferior section 936B or medial section 937B of hook-compatible fabric, providing effectively continuous variability in the location of the "origin" of the sling.

An example of a medial-to-lateral connection is depicted in "phantom" in FIG. 9A wherein sling 942 is coupled, at one end, to section 937B proximal to a superior location. The other end of the sling is coupled to section 940B. An example of an inferior-to-superior connection is depicted in phantom in FIG. 9A wherein sling 946 is coupled, at one end, to section 936B proximal to its mid-point and at the other end to section 938B. In both cases, the slings are pulled taut; that is, placed under tension, to provide an appropriate amount of support for the breast.

The use of one or both of these slings allows for highly-localized adjustments to breast geometry and an ability to ensure that there are no folds in breast tissue, as might otherwise occur for a woman with large, pendulous breasts.

FIG. 9B depicts an alternative embodiment of a sling, wherein strips 952B and 952B' of hook-and-loop fastener are attached to both sides of one end of sling 950. Strip 952A of hook-and-loop fastener is attached to one side of the other end of sling 950. Using cup 102A as an example, the end of sling 950 that includes one strip 952A of hook-and-loop fastener couples to section 937A of hook-compatible fabric. The other of the sling is positioned between closure 212A. Strip 952B of hook-and-loop fastener will couple to the hook-and-look fastener on one portion of closure 212A and strip 952B' will couple to the hook-and-loop fastener on the other portion of closure 212A. Closures 212A/B were included in bra 900 to illustrate the use of sling 950. In embodiments in which sling 950 is not used, a different type of lateral closure may suitably be used.

The slings depicted in conjunction with radiation treatment bra 900 can be used in conjunction with any of the bras discussed herein.

In some less preferred embodiments, the radiation treatment bra will include various adjustable elements, but neither medial nor lateral windows.

For example, a radiation bra in accordance with some less-preferred embodiments of the present teachings includes: a medial adjustable element, a lateral adjustable element, and a superior adjustable element, wherein both the medial and lateral adjustable elements are configured as closures. For the radiation treatment planning session, the patient would put on the bra and lie on the treatment table. Since neither the medial nor lateral windows are present, the medial adjustable closure is opened to separate the breast cups to enable the light field to be projected onto the chest for alignment/tattooing, etc. Likewise, the lateral adjustable closure is opened to project the light field onto the side(s) of the patient for alignment/tattooing. Even though both the medial and lateral closures are released, the breasts remain substantially covered by the cups, maintaining some modicum of privacy for the patient. After alignment is complete, the medial and lateral adjustable closures, as well as the superior adjustable element (which can be a closure, but need not be) are adjusted to establish the reference breast geometry. For regular radiation treatment sessions, the alignment is re-established with the medial and lateral closures released so that the tattoos (created during the planning session) can be aligned with the light fields. The medial and lateral closures are then adjusted, in accordance with the reference setting, to provide the reference geometry.

It should be clear from the foregoing disclosure and accompanying drawings that the present invention encompasses numerous different embodiments of a radiation treatment bra. A non-limiting list of embodiments in accordance with the present teachings includes a radiation treatment bra comprising:

(i) a medial window;
  (ii) a medial window and at least one adjustable element configured as a closure;
  (iii) a medial window and at least one adjustable element configured as a closure and comprising a measurement tool that provides an indicium of fit;
  (iv) a medial window and at least one adjustable element and a non-participating closure;
  (v) a medial window and two lateral windows;
  (vi) a medial window, two lateral windows, and at least one adjustable element configured as a closure;
  (vii) a medial window, two lateral windows, and at least one adjustable element and a non-participating closure;
  (viii) a medial adjustable element that comprises a medial window;
  (ix) a sling for providing additional support and positioning capability; and
  (x) a medial adjustable closure and a lateral adjustable closure, wherein both closures comprise a measurement tool that provides an indicium of fit.

Figure 10:
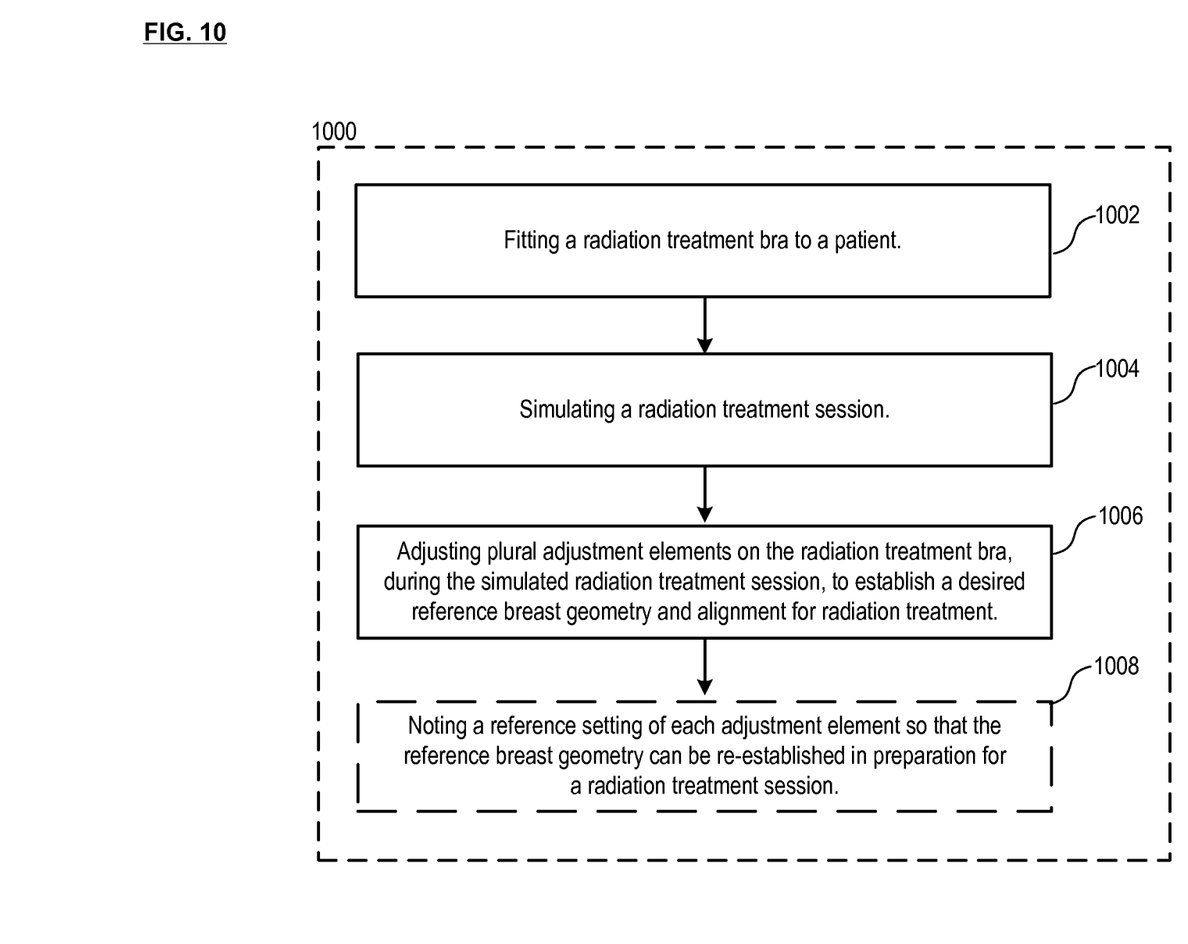
FIG. 10 depicts a flow diagram of a method in accordance with the present invention for establishing a reference breast geometry for a breast cancer patient undergoing radiation therapy.

FIG. 10 depicts method 1000 for establishing a reference breast geometry for a breast cancer patient undergoing radiation therapy.

Operation 1002 of method 1000 recites fitting a radiation treatment bra, such as radiation treatment bras 100, 200, and 400 through 900, to a patient. This involves selecting a radiation treatment bra having an appropriate cup size and back sizing (e.g., 36D, etc.).

Operation 1004 of method 1000 recites simulating a radiation treatment session for the patient. In this operation, the patient undergoes low-energy x-ray planning or CT simulation while in the treatment bra. During the simulation, iso-center check, and port-film verification (and while setting up each radiation treatment session), a light field is projected onto the patient's chest. (See, e.g., FIG. 1A). This operation also includes making temporary marks on the patient's chest to establish a reference alignment of the patient with respect to the light field, and hence the treatment machine.

Operation 1006 of method 1000 recites adjusting the plural adjustable elements (e.g., the medial adjustment element if present, lateral adjustment elements, and superior adjustment elements) to establish a reference breast geometry and alignment in accordance with the light field projected onto the patient's chest.

Optional operation 1008 of method 1000 recites memorializing (e.g., recording, marking, etc.) a reference setting for each adjustable element. In embodiments in which the radiation bra incorporates a non-participating closure, such as closure 118, which enables the bra to be removed/put-on without releasing the adjustable elements, operation 1008 is not required.

After the reference breast geometry and patient's alignment with respect to the treatment machine are confirmed, e.g., through a simulated radiation treatment session, the "temporary" marks are replaced by small alignment tattoos. This ensures that the patient will be positioned the same with respect to the treatment machine for each radiation treatment session. Depending upon the choice of material for the medial (and lateral) windows, tattoos can be made directly through the clear material without damaging the material or compromising tattoo location.

Figure 11:
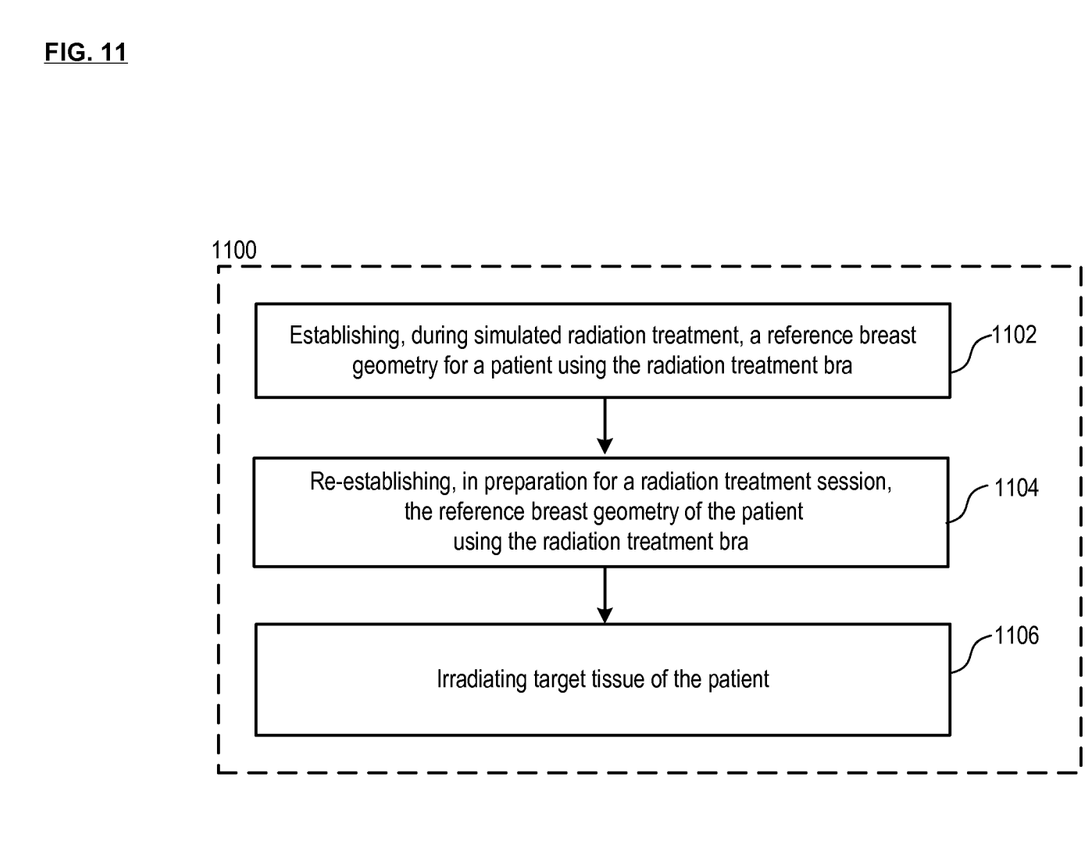
FIG. 11 depicts a flow diagram of a method for radiation therapy incorporating the method of FIG. 10.

FIG. 11 depicts method 1100, which is a method for radiation therapy that incorporates method 1000 for establishing a reference breast geometry, in accordance with the present invention.

Operation 1102 of method 1100 recites establishing, during simulated radiation treatment, a reference breast geometry for a patient using a radiation treatment bra, such as bras 100, 200, and 400 through 900. In some embodiments, this operation comprises method 1000; that is, operations 1002 through 1006 (and optionally 1008).

Operation 1104 of method 1100 recites re-establishing, in preparation for a radiation treatment session, the reference breast geometry of the patient using the radiation treatment bra. In some embodiments, this operation is performed by simply placing the radiation treatment bra on the patient and closing non-participating closure 118. In some other embodiments, this operation involves adjusting the adjustment elements, when they are embodied as closures, in accordance with their reference settings.

Operation 1106 of method 1100 recites irradiating the target tissue of the patient.

It is to be understood that although the disclosure teaches many examples of embodiments in accordance with the present teachings, many additional variations of the invention can easily be devised by those skilled in the art after reading this disclosure. As a consequence, the scope of the present invention is to be determined by the following claims.

What is claimed is:

1. A method comprising establishing a reference breast geometry for a breast cancer patient undergoing radiation therapy, wherein the reference breast geometry is established by:
    fitting a radiation treatment bra to a patient, wherein the bra has
        two cups consisting essentially of a stretch material, thereby enabling the cups to be readily deformable,
        a plurality of adjustable elements,
        and a medial window that is visually transparent and positioned so that a light field that is projected onto a wearer's chest for alignment purposes is viewable without obstruction by any portion of the bra;
    simulating a radiation treatment session for the patient; and
    establishing a desired reference breast geometry for subsequent radiation treatment sessions by deforming at least one of the cups to position and shape the patient's breast by adjusting the plurality of adjustable elements, wherein the adjustable elements are formed of a material that will not scatter or attenuate treatment radiation.

2. The method of claim 1 wherein the adjustable elements are closures, and wherein at least one of the adjustable elements comprises a measurement tool for providing an indicium of fit, and wherein the method further comprises memorializing a reference setting for the at least one adjustable element having the measurement tool.

3. The method of claim 2 further comprising removing the radiation treatment bra by releasing the at least one adjustable element having the measurement tool.

4. The method of claim 3 further comprising:
    positioning the radiation treatment bra on the patient in preparation for one of the radiation treatment sessions;
    re-establishing the reference breast geometry by referencing the memorialized reference setting and setting the at least one released closure to the reference setting; and
    irradiating target tissue of the patient.

5. The method of claim 4 further comprising:
    projecting, unobstructed by any portion of the bra, a light field onto the patient's chest; and
    aligning the patient with a radiation treatment machine by aligning, with the light field, marks that are formed on the patient's chest.

6. The method of claim 4 further comprising:
    projecting a light field through a lateral window of the radiation treatment bra onto a side of the patient's torso; and
    aligning the patient with a radiation treatment machine by aligning, with the light field, marks that are formed on the patient's side.

7. The method of claim 1 wherein the radiation treatment bra further comprises a non-participating closure, and wherein the method further comprises removing the radiation treatment bra, after the reference breast geometry is established, by releasing the non-participating closure, wherein removal is accomplished without altering the adjustment of any of the adjustable elements.

8. The method of claim 7 further comprising:
    positioning the radiation treatment bra on the patient in preparation for one of the radiation treatment sessions;
    re-establishing the reference breast geometry by closing the non-participating closure; and
    irradiating target tissue of the patient.

9. The method of claim 1 and further comprising coupling a sling to the at least one cup that covers a breast that is to be irradiated, wherein the sling is pulled taut to provide localized adjustment and supplement the adjustable elements in establishing the reference breast geometry.

10. The method of claim 9 wherein the sling is disposed in an orientation selected from the group consisting of medial-to-lateral, inferior-to-lateral, and inferior-to-superior.

11. A method comprising:
    establishing, during simulated radiation treatment, a reference breast geometry for a patient during simulated radiation treatment by deforming a non-rigid cup of a radiation treatment bra by adjusting a plurality of adjustable elements disposed on the radiation treatment bra;
    removing the radiation treatment bra;
    re-establishing, in preparation for one of a plurality of radiation treatment sessions, the reference geometry breast geometry of the patient using the radiation treatment bra; and
    irradiating target tissue of the patient.

12. The method of claim 11 wherein deforming a non-rigid cup of a radiation treatment bra further comprises obtaining a reference setting for each adjusted adjustable element, wherein the reference setting is the setting for each adjusted adjustable element that results in the reference breast geometry.

13. The method of claim 11 wherein removing the radiation treatment bra further comprises releasing at least one of the adjustable elements.

14. The method of claim 13 wherein re-establishing the reference breast geometry further comprises positioning the radiation treatment bra on the patient and setting the at least one released adjustable element to the reference setting thereof.

15. The method of claim 12 wherein removing the radiation treatment bra further comprises releasing a non-participating closure, wherein removal is accomplished without altering the reference setting of any adjusted adjustable element.

16. The method of claim 11 further comprising:
    projecting a light field onto the patient's chest through, in part, a medial window of the radiation treatment bra, wherein the projected light field projects a series of horizontal bars that extend vertically along a midline of the patient's torso, and wherein by virtue of the medial window, the projection of the light field onto the patient is not visually obstructed by any portion of the bra, and
    aligning the patient with a radiation treatment machine by aligning with the light field, marks that are formed on the patient's chest.

17. The method of claim 11 further comprising:
    projecting a light field through a lateral window of the radiation treatment bra onto a side of the patient's torso; and
    aligning the patient with a radiation treatment machine by aligning, with the light field, marks that are formed on the patient's side.

18. The method of claim 15 wherein re-establishing the reference breast geometry further comprises positioning the radiation treatment bra on the patient and closing the non-participating closure.

19. The method of claim 11 wherein deforming a non-rigid cup of a radiation treatment bra to establish a reference breast geometry further comprises coupling a sling to a breast cup of the radiation treatment bra that covers the target tissue, wherein the sling is pulled taut across the breast cup.

20. The method of claim 11 and further wherein adjusting a plurality of adjustable elements further comprises:
  adjusting a superior adjustable element disposed on at least one shoulder strap of the radiation treatment bra, and
  adjusting a lateral adjustable element disposed proximal to a lateral edge of the cup.

21. The method of claim 11 wherein establishing a reference breast geometry further comprises adjusting at least one medial adjustable element disposed proximal to a medial edge of at least one breast cup of the radiation treatment bra.

* * * * *